(12) United States Patent
Srinivas et al.

(10) Patent No.: US 7,518,012 B2
(45) Date of Patent: Apr. 14, 2009

(54) PROCESS FOR THE PREPARATION OF DIALKYL CARBONATE

(75) Inventors: Darbha Srinivas, Pune (IN); Rajendra Srivastava, Pune (IN); Paul Ratnasamy, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 553 days.

(21) Appl. No.: 11/394,136

(22) Filed: Mar. 30, 2006

(65) Prior Publication Data

US 2007/0083062 A1    Apr. 12, 2007

(30) Foreign Application Priority Data

Oct. 7, 2005    (IN) .................... 2721/DEL/2005

(51) Int. Cl.
    *C07C 69/96* (2006.01)
(52) U.S. Cl. .................... 558/277; 558/260
(58) Field of Classification Search ............ 558/260, 558/277
    See application file for complete search history.

(56) References Cited

U.S. PATENT DOCUMENTS

| | | | |
|---|---|---|---|
| 5,578,090 A | 11/1996 | Bradin | |
| 5,713,965 A | 2/1998 | Foglia et al. | |
| 6,015,440 A | 1/2000 | Noureddini | |
| 6,398,707 B1 | 6/2002 | Wu et al. | |
| 6,399,800 B1 | 6/2002 | Haas et al. | |
| 6,479,689 B1 | 11/2002 | Tojo et al. | |
| 6,642,399 B2 | 11/2003 | Boocock | |
| 6,696,583 B2 | 2/2004 | Koncar et al. | |
| 6,712,867 B1 | 3/2004 | Boocock | |
| 6,822,105 B1 | 11/2004 | Luxem et al. | |
| 6,835,858 B1 | 12/2004 | De Jonge et al. | |
| 6,855,838 B2 | 2/2005 | Haas et al. | |
| 7,211,681 B2 | 5/2007 | Furata | |
| 2005/0027137 A1 | 2/2005 | Hooker | |
| 2007/0004599 A1 | 1/2007 | Srinivas et al. | |
| 2007/0083056 A1 | 4/2007 | Srinivas et al. | |
| 2007/0083062 A1 | 4/2007 | Srinivas et al. | |
| 2007/0167642 A1 | 7/2007 | Oku et al. | |

FOREIGN PATENT DOCUMENTS

| WO | 00/05327 | 2/2000 |
|---|---|---|
| WO | 2004/048311 | 6/2004 |

*Primary Examiner*—Golam M Shameem
(74) *Attorney, Agent, or Firm*—Meyertons, Hood, Kivlin, Kowert & Goetzel, P.C.; Eric B. Meyertons

(57) ABSTRACT

The present invention provides a process for the preparation of dialkyl carbonates of general formula (1)

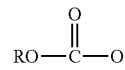

Formula 1 wherein R=alkyl ($C_1$-$C_8$) or $C_6H_5CH_2$
the said process comprises a reaction in between cyclic carbonate and alcohol, in the presence of a solid, double metal cyanide complex catalyst, at a temperature in the range of 140-180° C., for a period of 4-10 hrs, followed by the separation of catalyst from the above said reaction mixture by known methods to obtain the desired product.

9 Claims, No Drawings

PROCESS FOR THE PREPARATION OF DIALKYL CARBONATE

FIELD OF THE INVENTION

The present invention relates to a process for the preparation of dialkyl carbonates. Particularly, it relates to an eco-friendly, efficient process for producing of dialkyl carbonates of general formula (I).

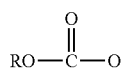

Formula 1 wherein R=alkyl ($C_1$-$C_8$) or $C_6H_5CH_2$

More particularly, the present invention relates to a process for the preparation of dialkyl carbonate from cyclic carbonate in the presence of double metal cyanide catalyst.

The solid, double metal cyanide catalyst, used in the present invention is described and disclosed in our co-pending Indian patent application No. 2723/DEL/2005.

BACKGROUND OF THE INVENTION

The dialkyl carbonates are precursors of bis-phenol-A-polycarbonate, a polymer known for its wide range of uses based upon its characteristics of transperancy, shock resistance and processability. They are important intermediates for the synthesis of fine chemicals, pharmaceuticals and plastics. Dialkyl carbonates also find applications as synthetic lubricants, solvents, plasticizes and monomers for organic glass. They are efficient alkylating agents and the processes using them are more eco-friendly compared to the conventional alkylation processes.

Conventionally, dialkyl carbonates and dimethyl carbonate in particular are synthesized using toxic chemicals like phosgene ($COCl_2$). Alternatively, they can be synthesized by oxidative carbonylation ($CO+O_2$) route using CuCl-base catalysts at high reaction temperatures. But this route is hazardous and produces corrosive hydrochloric acid. They are also produced from methanol by reacting with $NO+CO+O_2$ in the presence of a Pd/C catalyst. This route also bears a potential explosion problem. Toxic NO is main problem in the carbonylation of intermediate methylnitrile in this route (Encyclopedia of Chemical Processing and Design, Vol 40, Ed. by J. J. McKetta and W. A. Cunningham, Marcel Dekker Inc., New York, 1992, and Ulmann's encyclopedia of Industrial Chemistry, Vol. A 21, Ed. by B. Elvers, S. Hawkins and G. Schulz, 5th ed. VCH Verlagsgesellschaft, mbH, Germany 1992).

Synthesis of dialkyl carbonates by transesterification of cyclic carbonates with corresponding alcohols is an eco-friendly, non-toxic route. In recent times dialkyl carbonates especially dimethyl carbonate and dipropyl carbonates are commercially synthesized by this technology (Filtration Industry Analyst 1999 (Issue No. 27, June 1999) 2 and S. Fukuoka, M. Kawamura, K. Komiya, M. Tojo, H. Hachiya, K. Hasegawa, M. Aminaka, H. Okamoto, I. Fukawa, S. Konno, Green Chem. 5 (2003) 497). Other than mineral acids and alkali bases, compounds like metal alkoxides (aluminum isopropoxide, tetraalkoxytitanium, $(RO)Cu(PPh_3)_n$, PdMe($OCHCF_3Ph$(dpe)), organotin alkoxides etc.), non-ionic bases (amines, dimethylaminopyridine, guanidines etc.) and lipase enzymes are known to catalyze the transformation of cyclic carbonates to dialkyl carbonates. But these catalysts possess the drawback of unstability or difficulty in separating and reuse (J. Otera, Chem. Rev. 93 (1993) 1449).

There were efforts toward developing solid catalysts for preparing dialkyl carbonates. Tatsumi et al. (Chem. Commun. Year 1996, page 2281) reported the synthesis of dimethyl carbonates from ethylene carbonate and methanol using K-TS-1 as a solid base catalyst. The transesterification of dimethyl oxalate with phenol was reported recently by Ma et al., (Fuel Proc. Tech. Vol. 83, Year 2003, page 275). Srivatsava et al reported the application of titanosilicate catalysts (Catal. Today Vol. 93, Year 2004, page 127). In all these applications the efficiency of the solid catalysts and yield of dialkyl carbonate is rather low. Wei et al (Green Chem. Vol. 5, Year 2003, page 343; Catalysis of Organic Reactions Ed. By D. G. Morrell, Marcel and Decker Inc., New York, Year 2003, Chapter 58, page 659), Chu et al (Inorg. Chim. Acta Vol. 307, Year 2000, page 131), Watanabe and Tatsumi (Microporous Mesoporous Mater. Vol. 22, Year 1998, page 399) and Fang and Xiao (Separation and Purification Tech. Vol. 34, Year 2004, page 255) report the use of solid catalysts but yield of dialkyl carbonate is low (50 mol %). There were reports to synthesize dialkyl carbonates in a single-step process by reacting epoxides, $CO_2$ and alcohol over solid catalysts (Bhanage et al., Green Chem. Vol. 5, Year 2003, page 71; Appl. Catal. A: Gen Vol. 219, Year 2001, page 259; Chang et al., Appl. Catal. A: Gen Vol. 263, Year 2004, page 179; Jiang and Yang Catal. Lett. Vol. 95, Year 2004, page 127) but the yields of dialkyl carbonates are very poor. U.S. Pat. No. 6,835,858 describes the preparation of organic carbonates over Zn supported catalysts at 10° C., 25 bar pressure and space velocity WHSV=5 g/g/h. But the yield of dialkyl carbonate is low and leaching of Zn from the solid was detected. U.S. Pat. No. 6,479,689 tells a method for continuously producing of dialkyl carbonate and diol wherein dialkyl carbonate yields of 99% could be obtained but then catalyst separation was an issue. U.S. Pat. No. 6,392,078 details the synthesis of dimethyl carbonate from urea and methanol using homogenous tin alkoxide catalyst. U.S. Pat. No. 6,407,279 describes the synthesis from epoxide, monohydric alcohol and $CO_2$ using a homogeneous and heterogeneous catalyst. In other words, the prior art processes have one or more of the following disadvantages: (1) difficulties in catalyst separation, lower efficiency of the catalyst, catalyst stability during reaction, lower yields of dialkyl carbonates etc.

The present invention deals with a process, which eliminates all the above said drawbacks of the prior-art processes. It deals with production of dialkyl carbonates which comprises reacting of a cyclic carbonate with an alcohol over a solid, reusable double metal cyanide catalyst. One of the metals of the double metal cyanide catalyst is a Lewis acid metal ion such a $Zn^{2+}$ while the other is a basic metal ion such as Fe. Co-existence of Zn and Fe in the active site linking through cyano-bridges makes catalyst efficient to transform cyclic carbonates into dialkyl carbonates. The catalyst could be separated easily by centrifugation or simple filtration and reused in several recycling experiments with little loss in activity/selectivity. Most importantly, the catalyst is highly efficient and only a small amount (~5 wt % of cyclic carbonate) is needed to carryout the reaction. The process is atom-efficient and the reaction conditions like temperature and pressure are moderate.

OBJECTIVES OF THE INVENTION

The main objective of the present invention is to provide a process for production of dialkylcarbonate using an efficient heterogenous catalyst.

Another object of the present invention is to provide a process for the preparation of dialkyl carbonates from cyclic carbonates and alcohols in the presence of a solid catalyst in high selectivity and yields.

Yet another object is to describe a process for producing dialkyl carbonates at moderate reaction conditions.

SUMMARY OF THE INVENTION

Accordingly, the present invention provides a process for the preparation of dialkyl carbonate of general formula (I)

Formula 1

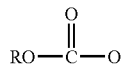

wherein R=alkyl ($C_1$-$C_8$) or $C_6H_5CH_2$ which comprises reacting a cyclic carbonate with an alcohol, in the presence of a solid, double metal cyanide complex catalyst, at a temperature in the range of 1400-180° C., for a period of 4-10 hrs, separating the catalyst from the above said reaction mixture by known methods to obtain the desired product.

In an embodiment of the present invention the molar ratio of cyclic carbonate to alcohol used is in the range of 1:8 to 1:12.

In yet another embodiment the cyclic carbonate used is selected from the group consisting of propylene carbonate, chloropropylene carbonate, ethylene carbonate and styrene carbonate.

In yet another embodiment the alcohol used is selected from the group consisting of methanol, ethanol, propanol, butanol, hexanol, octanol and benzyl alcohol.

In yet another embodiment the solid double metal cyanide complex catalyst used has a general formula:

wherein M is a transition metal ion; Zn and transition metal (M) are coordinated through cyanide bridging-groups; R is tertiary-butyl, x varies from 0 to 0.5, y varies from 3-5 and n is 10 or 12.

In yet another embodiment the basic transition metal ion, M used is Fe or Co.

In yet another embodiment the solid double metal cyanide complex catalyst used is easily separable from the reaction mixture and reusable in several recycling experiments without significant loss in activity.

In yet another embodiment the yield of dialkyl carbonate obtained by GC analysis is in the range of 60-100 mole %.

In yet another embodiment the yield of dialkyl carbonate obtained by column chromatography is in the range of 60-90 mole %.

DETAIL DESCRIPTION OF THE INVENTION

In the investigations leading to the present invention, it was found that the Fe—Zn double metal cyanide catalysts are highly efficient and could be easily separated from the products for further reuse. The prior art catalysts, mineral acid, alkali bases and lipases needed additional expenses and efforts for catalyst separation. An easily separable catalyst system e.g., the catalyst of the present invention is more advantageous. The solid catalyst of the present invention is not only efficient but avoids the tedious process of catalyst recovery characteristic of the prior art processes.

The solid double metal cyanide complex catalyst used comprises of Zn and another transition metal (M) coordinated through cyanide bridging-groups has the molecular formula:

wherein, M is a transition metal ion; x varies from 0 to 0.5, y varies from 3-5 and n is 10 or 12. R is tertiary-butyl, x varies from 0 to 0.5, y varies from 3-5 and n is 10 or 12 and the physico-chemical properties of which are described in Table-1.

TABLE 1

| Textural/Characteristics: | |
|---|---|
| Total surface area ($S_{BET}$) | 38.4 m²/g |
| External surface area ($S_{Exm.}$) | 24.1 m²/g |
| Micropore area | 14.3 m²/g |
| Average pore diameter | 3.9 nm |
| Total pore volume | 0.037 cc/g |
| Elemental analysis: | |
| % C-content | 23.3 |
| % H-content | 2.24 |
| % N-content | 17.3 |
| Morphology (SEM): | Spherical shaped particles |
| Spectral characteristics: | |
| FT-IR band positions (in cm⁻¹) | 2096 (n(C°N)), 1230 (n(C—O)), 500 (n(Fe C)) |
| Diffuse reflectance UV-visible bands (i nm) | 405, 330, 278, 236 and 208 |

The present invention is illustrated herein below with examples, which are illustrative only and should not be construed to limit the scope of the present invention in any manner.

EXAMPLE 1

This example illustrates the preparation of the solid, Fe—Zn double metal cyanide catalyst of the present invention. $K_4$[Fe(CN)$_6$] (0.01 mol) was dissolved in double distilled water (40 ml) (Solution-1). $ZnCl_2$ (0.1 mol) was dissolved in a mixture of distilled water (100 ml) and tertiary-butanol (20 ml) (Solution)-2. Poly(ethylene glycol)-block-poly(propylene glycol)-block-poly(ethylene glycol) (E0$_{20}$—PO$_{70}$-EO$_{20}$; molecular weight of about 5800) (15 g) was separately dissolved in 2 ml of distilled water and 40 ml of tertiary-butanol (Solution-3). Solution-2 was added to solution-1 over 60 min at 50° C. with vigorous stirring. White precipitation occurred during the addition. Then, solution-3 was added to the above reaction mixture over a period of 5 min and stirring was continued for further 1 h. The solid cake formed was filtered, washed with distilled water (500 ml) and dried at 25° C. This material was activated at 180-200° C. for 4 h prior to using it in the reactions.

EXAMPLE 2

This example describes the preparation of dimethyl carbonate from propylene carbonate and methanol. Propylene carbonate (1.02 g; 10 mmol), methanol (100 mmol), catalyst (250 mg) were charged in a 100 ml stainless steal autoclave having a Teflon-liner. The autoclave was closed and then placed in a rotating synthesis reactor (Hiro Co., Japan, Model-KH 02, rotating speed=30 rpm). The reaction was conducted at 170° C. for 8 h. The contents were allowed to cool to room temperature. Catalyst was separated by filtration from the reaction mixture. Then, the excess, unreacted alcohol was removed from the reaction mixture by distillation. The products were isolated by column chromatography (using petroleum ether: dichloromethane=1:1 and then with dichloromethane:methanol=95:5). The products were also analyzed by gas chromatography and identified by $^1$H NMR, FT—IR and GC—MS. Results are tabulated in table-2.

EXAMPLE 3

This example describes the preparation of dimethyl carbonate from propylene carbonate and methanol over Fe—Zn double metal cyanide catalyst at 140° C. Propylene carbonate (1.02 g; 10 mmol), methanol (100 mmol), catalyst (250 mg) were charged in a 100 ml stainless steal autoclave having a Teflon-liner. The autoclave was closed and then placed in a rotating synthesis reactor (Hiro Co., Japan, Model-KH 02, rotating speed=30 rpm). The reaction was conducted at 170° C. for 8 h. The contents were allowed to cool to room temperature. Catalyst was separated by filtration from the reaction mixture. The products were isolated and analyzed as described in EXAMPLE 2. Results are tabulated in table-2.

EXAMPLE 4

This example describes the preparation of dimethyl carbonate from propylene carbonate and methanol over Fe—Zn double metal cyanide catalyst at 180° C. Propylene carbonate (1.02 g; 10 mmol), methanol (100 mmol), catalyst (250 mg) were charged in a 100 ml stainless steal autoclave having a Teflon-liner. The autoclave was closed and then placed in a rotating synthesis reactor (Hiro Co., Japan, Model-KH 02, rotating speed=30 rpm). The reaction was conducted at 180° C. for 8 h. The contents were allowed to cool to room temperature. Catalyst was separated by filtration from the reaction mixture. The products were isolated and analyzed as described in EXAMPLE 2. Results are tabulated in table-2.

EXAMPLE 5

This example describes the preparation of diethyl carbonate from propylene carbonate and ethanol. Propylene carbonate (1.02 g; 10 mmol), ethanol (100 mmol), catalyst (250 mg) were charged in a 100 ml stainless steal autoclave having a Teflon-liner. The autoclave was closed and then placed in a rotating synthesis reactor (Hiro Co., Japan, Model-KH 02, rotating speed=30 rpm). The reaction was conducted at 170° C. for 8 h. The contents were allowed to cool to room temperature. Catalyst was separated by filtration from the reaction mixture. The products were isolated and analyzed as described in EXAMPLE 2. Results are tabulated in table-2.

EXAMPLE 6

This example describes the preparation of dipropyl carbonate from propylene carbonate and propanol. Propylene carbonate (1.02 g; 10 mmol), propanol (100 mmol), catalyst (250 mg) were charged in a 100 ml stainless steal autoclave having a Teflon-liner. The autoclave was closed and then placed in a rotating synthesis reactor (Hiro Co., Japan, Model-KH 02, rotating speed=30 rpm). The reaction was conducted at 170° C. for 8 h. The contents were allowed to cool to room temperature. Catalyst was separated by filtration from the reaction mixture. The products were isolated and analyzed as described in EXAMPLE 2. Results are tabulated in table-2.

EXAMPLE 7

This example describes the preparation of dibutyl carbonate from propylene carbonate and butanol. Propylene carbonate (1.02 g; 10 mmol), butanol (100 mmol), catalyst (250 mg) were charged in a 100 ml stainless steal autoclave having a Teflon-liner. The autoclave was closed and then placed in a rotating synthesis reactor (Hiro Co., Japan, Model-KH 02, rotating speed=30 rpm). The reaction was conducted at 170° C. for 8 h. The contents were allowed to cool to room temperature. Catalyst was separated by filtration from the reaction mixture. The products were isolated and analyzed as described in EXAMPLE 2. Results are tabulated in table-2.

EXAMPLE 8

This example describes the preparation of dihexyl carbonate from propylene carbonate and hexanol. Propylene carbonate (1.02 g; 10 mmol), hexanol (100 mmol), catalyst (250 mg) were charged in a 100 ml stainless steal autoclave having a Teflon-liner. The autoclave was closed and then placed in a rotating synthesis reactor (Hiro Co., Japan, Model-KH 02, rotating speed=30 rpm). The reaction was conducted at 170° C. for 8 h. The contents were allowed to cool to room temperature. Catalyst was separated by filtration from the reaction mixture. The products were isolated and analyzed as described in EXAMPLE 2. Results are tabulated in table-2.

EXAMPLE 9

This example describes the preparation of dibenzyl carbonate from propylene carbonate and benzyl alcohol. Propylene carbonate (1.02 g; 10 mmol), benzyl alcohol (100 mmol), catalyst (250 mg) were charged in a 100 ml stainless steal autoclave having a Teflon-liner. The autoclave was closed and then placed in a rotating synthesis reactor (Hiro Co., Japan, Model-KH 02, rotating speed=30 rpm). The reaction was conducted at 170° C. for 8 h. The contents were allowed to cool to room temperature. Catalyst was separated by filtration from the reaction mixture. The products were isolated and analyzed as described in EXAMPLE 2. Results are tabulated in table-2.

EXAMPLE 10

This example describes the preparation of dimethyl carbonate from propylene carbonate and methanol over used (in 5 recycling experiments) Fe—Zn double metal cyanide catalyst. Propylene carbonate (1.02 g; 10 mmol), methanol (100 mmol), catalyst (250 mg) were charged in a 100 ml stainless steal autoclave having a Teflon-liner. The autoclave was closed and then placed in a rotating synthesis reactor (Hiro Co., Japan, Model-KH 02, rotating speed=30 rpm). The reaction was conducted at 170° C. for 8 h. The contents were allowed to cool to room temperature. Catalyst was separated by filtration from the reaction mixture. The products were isolated and analyzed as described in EXAMPLE 2. Results are tabulated in table-2.

TABLE 2

| EXAMPLE NO. | Catalyst | Alcohol | Reaction temperature (° C.) | Dialkyl carbonate yield by G analysis (mol %) | Dialkyl carbonat yield - Isolated b column chromatography) (mol %) |
|---|---|---|---|---|---|
| 2 | Fresh | Methanol | 443 | 100 | 86.6 |
| 3 | Fresh | Methanol | 413 | 64 | 53.3 |
| 4 | Fresh | Methanol | 453 | 100 | 88.0 |
| 5 | Fresh | Ethanol | 443 | 92 | 79.4 |
| 6 | Fresh | Propanol | 443 | 88 | 77.5 |
| 7 | Fresh | Butanol | 443 | 81 | 69.3 |
| 8 | Fresh | Hexanol | 443 | 74 | 62.5 |
| 9 | Fresh | Benzyl alcohol | 443 | 90 | 77.8 |
| 10 | Used (in 5 re-cycles) | Methanol | 443 | 100 | 82.6 |

Advantages of the Present Invention are:
1. The process described above has the combined unique advantages of high conversion accompanied with high selectivity for alkyl carbonates.
2. The process of the present invention leads to the synthesis of dialkyl carbonates by an eco-friendly, non-hazardous route avoiding the using of toxic-chemicals like phosgene.
3. The catalyst could be easily separated from the product mixture and reused in several recycling experiments without significant loss in activity/selectivity.

We claim:

1. A process for the preparation of dialkyl carbonate of general formula (1)

Formula 1

Wherein R=alkyl ($C_1$-$C_8$) or $C_6H_5CH_2$

Which comprises reacting a cyclic carbonate with an alcohol, in the presence of a solid, double metal cyanide complex catalyst, at a temperature in the range of 140°-180° C., for a period of 4-10 hrs, separating the catalyst from the above said reaction mixture by known methods to obtain the desired product.

2. A process as claimed in claim 1, wherein the molar ratio of cyclic carbonate to alcohol used is in the range of 1:8 to 1:12.

3. A process as claimed in claim 1, wherein the cyclic carbonate used is selected from the group consisting of propylene carbonate, chloropropylene carbonate, ethylene carbonate and styrene carbonate.

4. A process as claimed in claim 1, wherein the alcohol used is selected from the group consisting of methanol, ethanol, propanol, butanol, hexanol, octanol and benzyl alcohol.

5. A process as claimed in claim 1, wherein the solid double metal cyanide complex catalyst used has a general formula:

$$Zn_3M_2(CN)_n(ROH).xZnCl_2.yH_2O$$

wherein M is a transition metal ion; Zn and transition metal (M) are coordinated through cyanide bridging-groups; R is tertiary-butyl, x varies from 0 to 0.5, y varies from 3-5 and n is 10 or 12.

6. A process as claimed in claim 5, wherein the basic transition metal ion, M used is Fe or Co.

7. A process as claimed in claim 1, wherein the solid double metal cyanide complex catalyst used is easily separable from the reaction mixture and reusable in several recycling experiments without significant loss in activity.

8. A process as claimed in claim 1, wherein the yield of dialkyl carbonate obtained by GC analysis is in the range of 60-100 mole %.

9. A process as claimed in claim 1, wherein the yield of dialkyl carbonate obtained by column chromatography is in the range of 60-90 mole %.

* * * * *